(12) United States Patent
Lundquist et al.

(10) Patent No.: US 10,092,864 B2
(45) Date of Patent: Oct. 9, 2018

(54) APPARATUS FOR PREPARING A MULTI-LAYERED BLOOD PRODUCT BY CENTRIFUGATION

(75) Inventors: Rasmus Lundquist, Bronshoj (DK); Niels Erik Holm, Birkerod (DK)

(73) Assignee: REAPPLIX APS, Birkerod (DK)

( * ) Notice: Subject to any disclaimer, the term of this patent is extended or adjusted under 35 U.S.C. 154(b) by 5 days.

(21) Appl. No.: 13/811,114

(22) PCT Filed: Sep. 20, 2011

(86) PCT No.: PCT/DK2011/050354
§ 371 (c)(1),
(2), (4) Date: Jan. 18, 2013

(87) PCT Pub. No.: WO2012/037942
PCT Pub. Date: Mar. 29, 2012

(65) Prior Publication Data
US 2013/0140226 A1   Jun. 6, 2013

(30) Foreign Application Priority Data

Sep. 20, 2010 (DK) .................................. 2010 00841

(51) Int. Cl.
*B01L 3/00* (2006.01)
*B01D 21/26* (2006.01)
(Continued)

(52) U.S. Cl.
CPC ........... *B01D 21/262* (2013.01); *A61M 1/029* (2013.01); *A61M 1/3633* (2013.01); *B01L 3/50215* (2013.01); *A61M 1/3693* (2013.01); *B01L 2200/0689* (2013.01); *B01L 2300/044* (2013.01); *B01L 2300/0609* (2013.01); *B01L 2300/0672* (2013.01); *B01L 2300/0681* (2013.01); *B01L 2400/0409* (2013.01)

(58) Field of Classification Search
CPC ....... B01L 3/50; B01L 3/5021; B01L 3/50215
USPC ........ 422/405, 534, 535, 547, 548, 549, 550
See application file for complete search history.

(56) References Cited

U.S. PATENT DOCUMENTS 3,814,248 A * 6/1974 Lawhead ............ B01L 3/50215
210/117
3,894,952 A 7/1975 Ayres
(Continued)

FOREIGN PATENT DOCUMENTS

EP       1006359 A2    6/2000
EP       1006360 A2    6/2000
(Continued)

*Primary Examiner* — Jill Warden
*Assistant Examiner* — Dwayne K Handy
(74) *Attorney, Agent, or Firm* — Nath, Goldberg & Meyer; Jerald L. Meyer; Stanley N. Protigal (57) ABSTRACT

Container to be used for preparing a multi-layered blood product by centrifugation, said container comprising a substantially cylindrical body (2) with a closed bottom (3) and a top (4) having a filling opening as well as a filter device (15), which is slidable inside the container (1). The filing opening is closed by means of a penetrable membrane (13), and the filter device (15) comprises a substantially planar mesh (16) and a supporting buoyancy body (18). In addition to this, there are means (35, 36, 39, 40, 42), for releasable fixation of the filter device (15) adjacent to the bottom (3) of the container (1).

20 Claims, 4 Drawing Sheets

(51) Int. Cl.
*A61M 1/36* (2006.01)
*A61M 1/02* (2006.01)

(56) References Cited

U.S. PATENT DOCUMENTS

| | | | | |
|---|---|---|---|---|
| 4,832,851 | A | * | 5/1989 | Bowers .................. B01D 33/00 210/321.67 |
| 5,455,009 | A | * | 10/1995 | Vogler .................. G01N 33/491 422/548 |
| 7,220,593 | B2 | * | 5/2007 | Haubert ............. B01L 3/50215 210/782 |
| 2006/0257465 | A1 | | 11/2006 | Maurer et al. |
| 2008/0023414 | A1 | | 1/2008 | Konrad |
| 2008/0283474 | A1 | | 11/2008 | Leach et al. |
| 2010/0155319 | A1 | | 6/2010 | Felix et al. |

FOREIGN PATENT DOCUMENTS

| | | |
|---|---|---|
| JP | 727578 U | 5/1995 |
| WO | 03/092894 A2 | 11/2003 |
| WO | 2010/020254 A1 | 2/2010 |
| WO | 2010020247 A1 | 2/2010 |

* cited by examiner

APPARATUS FOR PREPARING A MULTI-LAYERED BLOOD PRODUCT BY CENTRIFUGATION

This is a National Phase Application filed under 35 U.S.C. 371 as a national stage of PCT/DK2011/050354, filed Sep. 20, 2011, and claiming the benefit from Danish Application No. PA 2010 00841, filed Sep. 20, 2010, the content of which is hereby incorporated by reference in its entirety.

TECHNICAL FIELD

The present invention relates to a container to be used for preparing making a multi-layered blood product by centrifugation, said container comprising a substantially cylindrical body with a closed bottom and a top having a filling opening as well as a filter device, which is slidable inside the container.

BACKGROUND

WO 2010/020254 discloses how to prepare a multi-layered blood product by centrifugation of blood. First, the blood is placed in a container, and the coagulation of the blood is activated during or after placing the blood in the container. During the centrifugation, the components of the blood are separated from each other and produce a three-layered blood product, which in sequential order comprises a first layer, which substantially comprises fibrin, a second, intermediate layer, which substantially comprises thrombocytes, and a third layer, which substantially comprises leukocytes. This three-layered blood product forms a coherent pad, which is separated from serum and erythrocytes. The blood product or the blood pad is suitable for the treatment of wounds. By placing the third layer closest to the wound, the wound is kept substantially aseptic as the leukocytes of the third layer counter infection and attract other cells including macrophages. The second layer substantially comprising thrombocyte contains growth-promoting factors, which stimulate the healing of the wound, whereas the third layer, which comprises substantially fibrin, offers an effective protection against contamination from the surroundings, just as the content of growth-promoting factors of the first layer is released in time. The blood product in question is suitable for autogenic use. Due to a large internal strength, density towards liquids and gasses, the blood product is also suitable for use in other surgical procedures, such as anastomosis, hernioplasties and orthopaedics.

US 2008/0023414 discloses a container unit for separating blood into a lighter and a heavier constituent by centrifugation. The container unit comprises a tubular body with an interior, a closed bottom and an open top closed by means of a closure. The inner dimension of the tubular body slightly tapers as seen from the top toward the bottom. A separating device is arranged in the interior of the tubular body at the top thereof. The separating device is circumferentially deformable and engages sealingly to the inner surface of the tubular body. When using the container unit, blood is introduced into the interior below the separating device. When the separating device is subjected to centrifugation the separating device moves downwards towards the bottom until it has moved a preselected distance. The lighter constituent flows upwards through the separating device to be situated above the separating device while the heavier constituent is situated below the separating device.

US 2010/0155319 discloses a separation assembly for separating a fluid such as blood into a heavier fraction and a lighter fraction. The separation assembly comprises a tubular body having a closed bottom end and an open upper end closed by a closure. A separator is displaceably arranged in the interior of the tubular body. The separator comprises a float and ballast, the float and ballast being connected by bellows sealingly engaging the inner surface of the tubular body when not being subjected to centrifugal force. The overall density of the separator is between that of the heavier and lighter fraction. When using the separation assembly, blood is introduced into the interior of the tubular body below the separator, the separator being initially situated at the top end adjacent the closure. When subjected to centrifugation, the diameter of the bellows decreases and the separator moved downwards toward the bottom until it, due to its overall density, is situated between the lighter and the heavier fraction, the lighter fraction being situated above and the heavier fraction below the separator.

DISCLOSURE OF THE INVENTION

The object of the invention is to provide a container, which is especially suitable for use when preparing said blood product.

According to the invention, this is achieved by filling opening being closed by a penetrable membrane, that the filter device comprises a substantially planar mesh and a supporting buoyancy body, and that means are provided for releasable fixation of the filter device adjacent to the bottom of the container.

This container allows for providing of a vacuum in the interior thereof before use. The penetrable membrane allows for easy filling of the container with blood directly from a person, who is to use the blood product. A double needle may be used for the filing, i.e. a needle, which has a cutting edge in both ends, often produced as a thin tube with a needle in both ends. At the same time, the vacuum ensures that the blood is subjected to forces, which may promote the necessary coagulation process, if necessary in combination with the material of which the container is made. The substantially planar mesh of the filter device provides a collecting surface for the blood product during the centrifugation whilst at the same time, heavier parts of the blood, which are still floating, can flow through the mesh down beneath said mesh as the centrifugation is carried out with the bottom of the container facing away from the axis of rotation of the centrifuge. When the blood product has collected above or on the mesh of the filter device, the filter device is appropriately released when stopping the centrifugation or during the subsequent resumption of the centrifugation. This means that the filter device carrying the blood product moves upwards in the container during passing of the liquid blood component, which was situated above the filter device in the container prior to the release of the filter device. When the blood product has moved upwards to the surface of the liquid component in the container, the centrifugation is stopped and the blood product appropriately removed by means of forceps after opening the container appropriately by removing the top. The use of a filter device for collecting the blood product reduces the centrifugation time and the forces compared to a centrifugation without a filter device. The removal of the blood product is facilitated by a filter device with a buoyancy body, which is arranged such that during the centrifugation, the blood product during the continued centrifugation is lifted to the surface of the liquid in the container. The blood product has such strength that it may be removed by means of forceps and applied at a desired spot, e.g. on a wound.

According to the invention, the filling opening may have a transverse wall placed between the membrane and the inside of the container and having a small passage. Thereby, the blood is subjected to especially great transverse forces during the filling of the container and the presence of a vacuum in the inside of the container. These transverse forces promote the initiation of the coagulation process.

Furthermore, according to the invention, the penetrable membrane may have an annular, protruding and plug-like part at the bottom surface thereof, said plug-like part being adapted to face the inside of the container, and that at the side facing the membrane, the transverse wall has an annular flange extending around the passage and interacting with the protruding plug-like part of the membrane in a tight-fitting way.

According to the invention, the filling opening may have a transverse wall placed between the membrane and the inside of the container, said transverse wall having a relatively small, penetrable wall thickness. The small wall thickness prevents the needle from being blocked during penetration of the needle of the blood collection set. This wall thickness will depend on the material used. If the membrane is made of Polypropylene, the membrane thickness is preferably less than 0.5 mm. The advantage of the transverse wall without a passage is that the material used will be less permeable than penetration membranes, which are typically made of rubber materials and relatively permeable. In order to ensure a stabile vacuum over time, a membrane of a sealing material will be an advantage.

In addition to this, according to the invention, the substantially planar mesh (16) of the filter device may have a downwardly extending skirt, and the buoyancy body is a closed capsule, which is received in the cavity defined by the skirt, and that spacing means are provided for fixing the capsule in a distance from both the bottom surface of the mesh and the inner surface of the skirt. Thereby, an especially easy way is achieved for the filter device to move easily in a free-flowing state inside the container to the surface of the liquid present in the container. The spacing means ensure that the liquid flowing through the filter device during centrifugation can pass the capsule easily and thereby through the filter device during the centrifugation process.

Advantageously, the spacing means between the mesh and the buoyancy body may be radially extending ribs or rods at the bottom surface of the mesh. Advantageously, these ribs or rods are formed integrally with the mesh.

Furthermore, the spacing means between the buoyancy body and the skirt may be projections at the lateral face of the buoyancy body and are formed with evenly distributed distances relative to each other along the circumference of the buoyancy body. Advantageously, these projections may be formed integrally with the buoyancy body.

According to the invention, the capsule forming the buoyancy body is formed by two flat-bottomed bowls engaging each other in a telescope-like way with the bottoms facing away from each other, sealing means being provided for tightly sealing the two bowls together. Thereby, an especially simple and easily manufactured capsule is achieved.

According to the invention, along the periphery, the skirt of the filter device may have a number of yielding flaps arranged interspaced and each having a radial protruding projection for frictional interaction with the inner face of the container, whereby a good fixation of the filter device is achieved at the bottom of the container before use.

More appropriately, according to the invention, the container with bottom and top may be rotationally-symmetrically shaped around the longitudinal axis of the cylindrical body, and that the top and the cylindrical body including the bottom are separately formed parts, said parts being adapted to be close-fittingly coupled.

More appropriately, according to the invention, the mesh of the filter device including the skirt may be integrally formed.

According to the invention, the means for releasable fixation of the filter device adjacent to the bottom of the container may comprise two cups adapted to be inserted into each other with the mouths facing in the same direction, and where the inner cup is provided with holes for reception of respective slidable squeeze pin extending radially inwardly, the outermost ends of the squeeze pins being adapted to cooperate in a cam follower-like way with the edge of the outer cup when the cups are inserted into each other, whereas the inner most ends of the squeeze pins are adapted to press the wall of the container radially inwards when placing the container with the filter device in the inner cup and thereby fix the filter device in close proximity of the bottom of the container until the two cups are pulled away from each other again. Thereby, an especially simple way for fixation of the filter device at the bottom of the container is achieved as long as desired during the centrifugation.

Especially appropriate, according to the invention, outer cup may be adapted to be a fixed part of a holder for reception of the container during the centrifugation, and that the cups are telescoped under the influence of the centrifugal force during the centrifugation. Subsequently, the release of the filter device takes place by removing the container with the inner cup from the outer cup and thereafter, the container is placed in the outer cup again without the inner cup with the pins or alternatively with a stabilising second cup without pins.

Especially appropriate, spring means may be provided between the two cups for moving them automatically away from each other again when stopping the centrifugation, whereby the release of the filter device takes place automatically.

According to the invention, the inside wall of the outer cup may be provided with at least one groove for co-operation with a guide pin on the inner cup, so that the inner cup is turned a first distance during a telescoped movement of the cups and a subsequent displacement of the cups in a direction away from each other again during a first centrifugation phase and is turned a second distance during a second telescoped movement during a subsequent centrifugation phase, and in that in the end, the squeeze pins are placed opposite each their groove in the outer cup, such that they are released and remain unaffected during a continued centrifugation of the container. Thereby, the release or disengaging of the filter device follows completely automatically simply by stopping the centrifugation, and the centrifugation may be continued without the filter device being retained at the bottom of the container.

Furthermore, according to the invention, the squeeze pins may be designed to function as guide pins while interacting with corresponding grooves in the outer cup.

Furthermore, according to the invention, at a level above the mesh, the filter device may carry an easily releasable reinforcement means for the blood product, whereby the inside of the blood product is provided with a reinforcement means, which may function as a reinforcement of the blood product and if desired, be used in connection with a possible sewing on of the blood product to the place of use.

Finally, according to the invention the reinforcement means may be fixed by means of gravity, whereby it is released especially easy from the filter device by removing the filter device.

BRIEF DESCRIPTION OF THE DRAWING(S)

The invention is explained in detail below with reference to the drawings, in which.

DETAILED DESCRIPTION OF THE INVENTION

Figure 1:
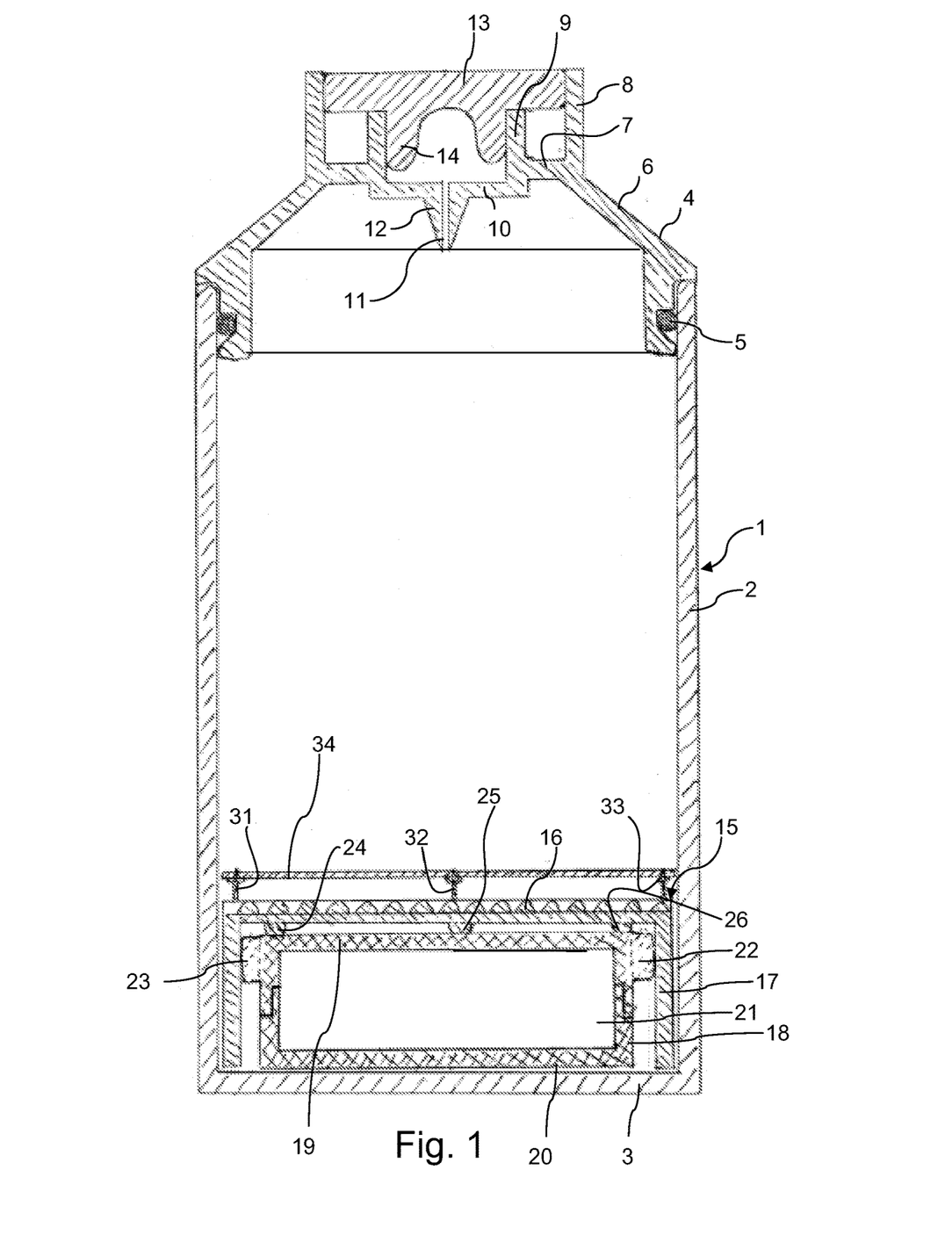
FIG. 1 shows a cross section of an embodiment of a container according to the invention.

The container shown in FIG. 1, which is provided with the general reference number 1, comprises a rotational-symmetrical, cylindrical body 2 made in one piece with a bottom 3. At the top or at the other end, the cylindrical body 2 is closed by means of a detachable top 4, which is tightly sealed to the cylindrical body 2 by means of a seal 5. The top 4 is also rotationally-symmetrically formed and has a truncated cone-shaped wall 6, which, in the direction way from the cylindrical body 2, extends into an annular, radially extending wall 7, which is delimited by two annular, axially extending flanges 8 and 9, of which the outer flange 8 has a slightly longer axial direction than the inner flange 9. At the bottom, the inner flange 9 is formed integrally with a radially extending wall 10 being centrally provided with an axially extending narrow passage 11 and ending on the surface facing the inside of the container 1 in a substantially truncated cone-shaped projection 12 formed integrally with the radial wall 10. At the top, the top 4 carries a circular, penetrable membrane 13 substantially formed as a disc, but on the one side having an annular protruding part 14, which interacts with the inner flange 9 at the top 4 in a plug-like way. Along the inner side of the outer flange 8, the membrane 13 abuts the outer flange 8 tight-fittingly at the top 4. It may be received in an annular recess in the outer flange 8 (not shown).

Inside the container 1, there is a loosely fitted filter device shown by the general reference number 15. At the top, it comprises a grid or mesh-shaped part 16, which is formed integrally with an annular skirt 17. In the cavity defined by the skirt 17, a capsule-shaped buoyancy body 18 is received, which is formed by two joined cups 19 and 20 formed such that they define a cavity 21 tight-fittingly, if necessary by using an intermediate sealing ring (not shown). Along the periphery of the buoyancy body 18, projections 22 and 23 are formed with appropriate distance from each other, which maintain the buoyancy body 18 in a distance from the skirt 17 but frictionally engaged therewith. The buoyancy body 18 is also maintained in an appropriate distance from a grid or mesh-shaped part 16 by means of projections 24, 25 and 26, which are formed as one piece with the grid or mesh-shaped part 16.

Figure 3:
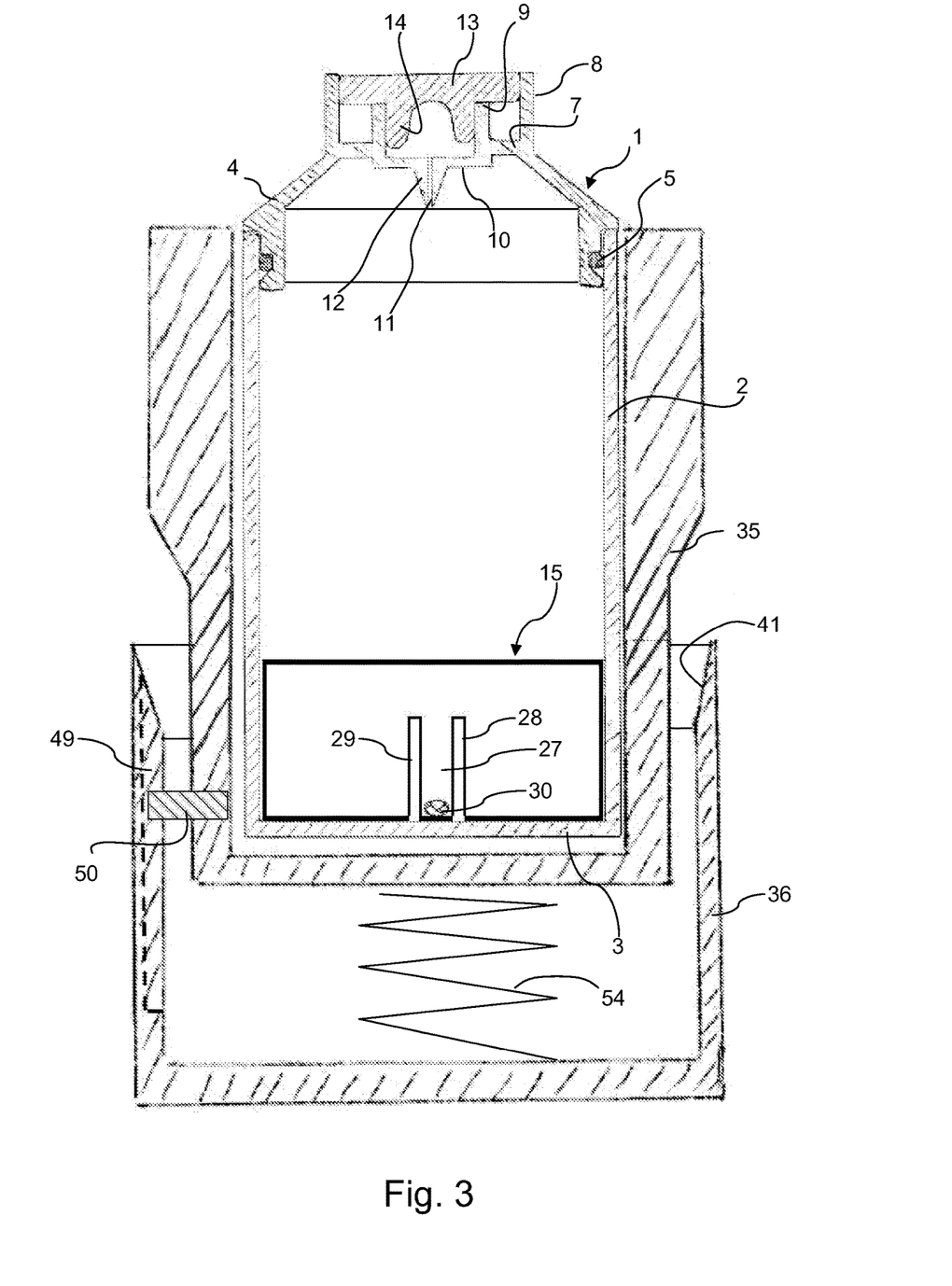
FIG. 3 is the same as FIG. 2, but seen in another diagonal section and with the filter device being shown schematically, and viewed from the side.

Along the skirt 17, yielding flaps 27 are formed with appropriate distances from each other by means of axially extending apertures 28 and 29 (see FIG. 3). The flaps 27 between the two apertures 28 and 29 have a projection 30 at the free end, which protrudes in a radial direction. As a result of the projections 30 abutting the inner side of the cylindrical body, these flanges 27 with projections 30 allow for fixation of the filter device 15 at the bottom of the container 1 during transportation. This fixation is achieved by means of friction only.

In the embodiment shown in FIG. 1, upwardly protruding holding means 31, 32 and 33 are formed with appropriate distances from each other at the top of the grid or mesh-shaped part 16 of the filter device 15, said protruding holding means 31, 32 and 33 being adapted to support a reinforcement mesh 34, which is appropriately carried by abutting contact faces on the holding means 31, 32 and 33 due to gravity and is in frictional engagement with the holding means 31, 32 and 33.

Figure 2:
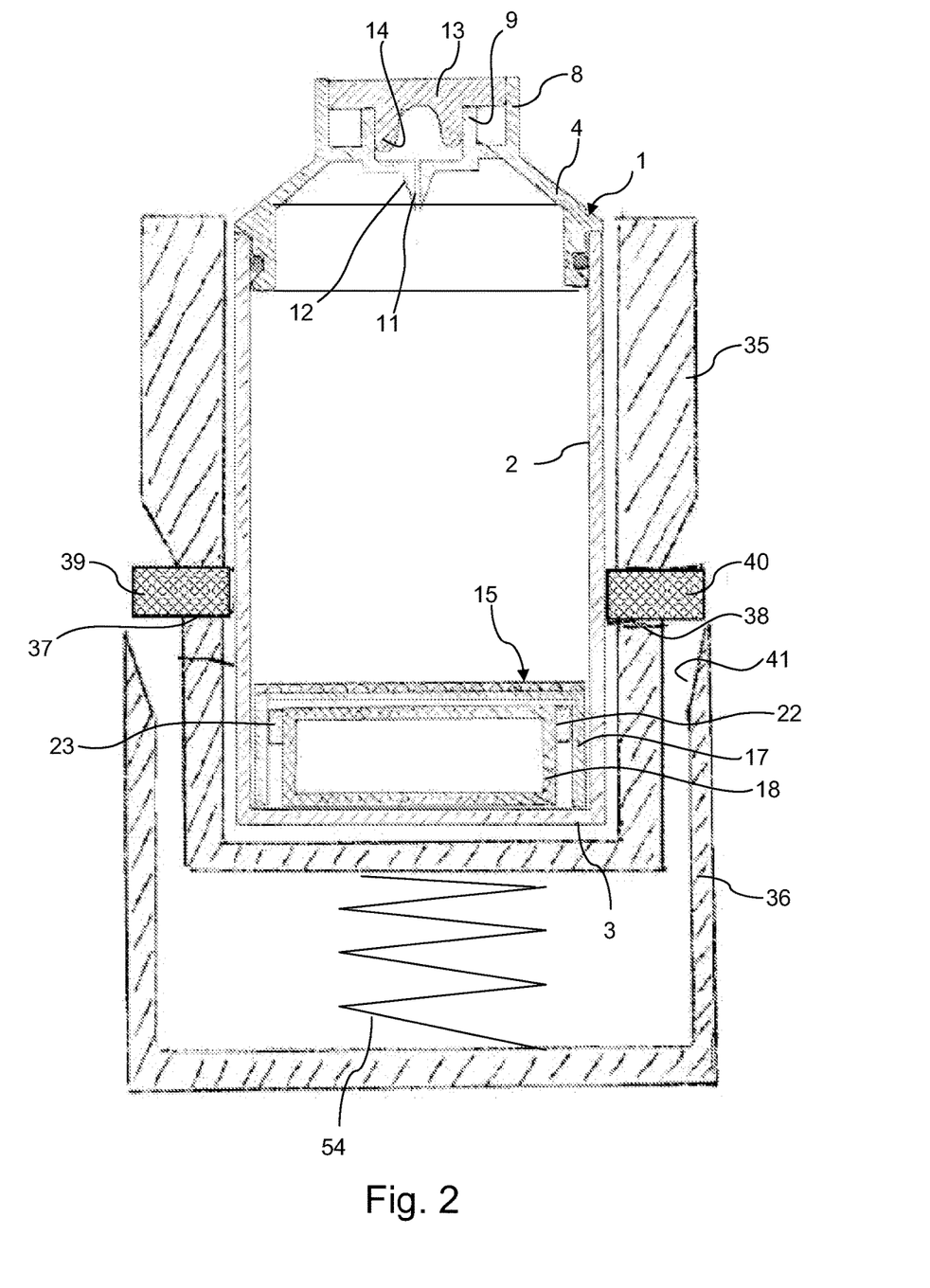
FIG. 2 shows a cross section of another embodiment of a container according to the invention placed in an inner and an outer cup for fixation of the filter device at the bottom of the container.

In FIG. 2, the container 1 is shown in an embodiment without a reinforcement mesh, but with means for releasable fixation of the filter device 15 at the bottom of the container 1 during a centrifugation process. These means comprise two cups, an inner cup 35 and an outer cup 36, which are formed to be able to be inserted into each other with the mouth facing in the same direction. In a level along the circumference of the inner cup 15, appropriately spaced holes 37 and 38 are formed for reception of their respective squeeze pin 39 and 40, adapted to be fixed by means of friction in the respective holes 37 and 38 in the embodiment shown.

The outer cup 36 has a slanting surface 41 along the upper edge for interaction with the squeeze pins 39 and 40 during telescoping of the cups, the slanting surface 41 displacing the squeeze pins radially inwards in a cam follower-like way. The two cups 35 and 36 are formed in such a way that they may be easily displaced in a direction towards each other and away from each other. The displacement away from each other may be facilitated by means of a schematically shown spring 54. The pins 39 and 40 are dimensioned in such a way that they push the wall of the cylindrical body 2 of the container 1 somewhat inwards to such an extent that the filter device 15 is fixed at the bottom of the container 1 during the use thereof.

Appropriately, the outer cup 36 may be a fixed cup in a centrifuge such that during centrifugation, the container 1 is placed therein together with the inner cup 35 and pressed down towards the bottom of the outer cup 36 during centrifugation.

The container according to the invention is used in the following way. At an appropriate point in time before the container 1 is brought into use, vacuum is established in the container 1 in an appropriate way. When using the container 1, the membrane 13 is penetrated with a needle, which is connected to a human vein via an appropriate pipe. Assisted by the vacuum in the container 1, the blood flows into the cavity under the membrane 13 at the top 4 of the container 1, from where it is sucked through the relatively narrow passage 11 and into the inside of the container 1 as the vacuum therein subjects the blood to large shear forces in the passage, whereupon the blood is sprayed into the interior of the container 1. Thereby, the initiation of the coagulation process of the blood is facilitated, possibly further facilitated by means of the material, of which the container 1 is made. When the container 1 has been supplied with an appropriate amount of blood, the needle is removed from the membrane 13, and the container 1 is placed in the inner cup 35.

Together with the inner cup 35, it is placed in the outer cup 36 in a centrifuge. When the centrifugation is started, the inner cup 35 is pressed down towards the bottom of the outer cup 36, normally at the same time as the axis of the container is moved into a horizontal or radial position relative to the axis of rotation of the centrifuge.

During the centrifugation, as mentioned above, the three-layered blood product is produced after an appropriate amount of time (e.g. 8 minutes) and an appropriate application of force. Thereafter, the centrifuge is stopped and the squeeze pins 39, 40 are removed, whereupon the centrifugation is resumed. As a result of removing the squeeze pins 39 and 40, the filter device 15 can now move upwards towards the surface of the liquid, especially as a result of the presence of the buoyancy body 18. Thereby, the blood product is moved upwards, whereas the surrounding liquid passes through and past the filter device down towards the bottom of the container 1. When, or a short time after, the filter device has reached the surface of the liquid at the top of the container, or has been stopped when reaching the top 1, the centrifugation is stopped and the container is removed from the centrifuge. Thereafter, the top 4 is removed from the upper part of the container 1, and the blood product is now ready to be removed from the container and placed on the desired spot on a patient.

In connection with the presence of the reinforcement mesh shown in FIG. 1, this will, with an appropriate placement on the filter device 15, be placed on an appropriate place in the blood product, e.g. in the first layer, which comprises mainly fibrin as this layer is the strongest layer.

Figure 4:
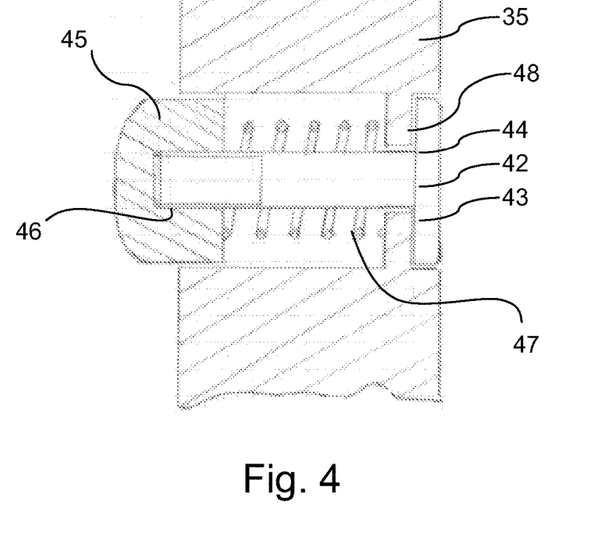
FIG. 4 is a cross sectional view showing a squeeze pin.

Instead of having to remove the squeeze pins manually, they may be preloaded in a direction radially outwards relative to the inner cup. For example, the squeeze pins may be formed as shown in FIG. 4, which shows a section of the inner cup 35, seen in a large scale and with a squeeze pin 42 comprising a bolt-like part 43, the head 44 of said bolt-like part facing towards the inside of the cup, and a nut 45 having a threaded blindhole supplied with a thread for reception of the bolt 43. The bolt-like part 43 has a rounded surface for interaction with the slanting surface 41 on the outer cup. By means of a spring 47, the squeeze pin 42 is preloaded in a position in which the head 44 is aligned with the inside of the cup 35. Here, the bolt 44 abuts an annular stop face 48 integrally formed with the cup 35.

As soon as the outer cup 36 no longer presses the squeeze pin 42 towards the container 1 in the inner cup 35, the head 44 of the pin 42 is pulled away from its engagement with the container 1.

Figure 5:
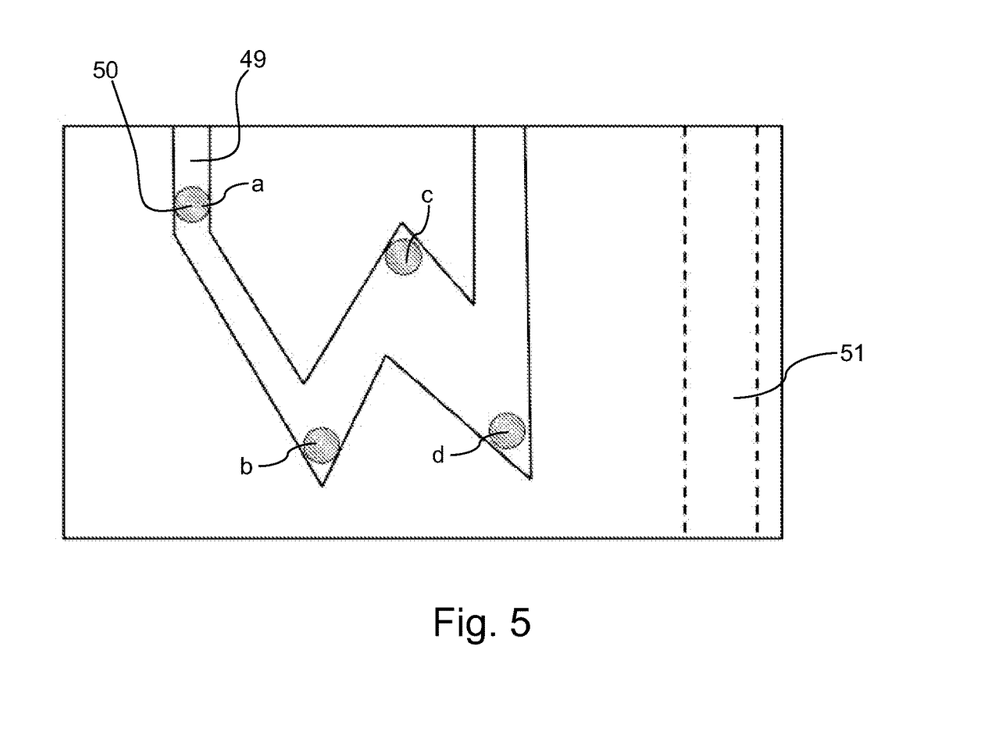
FIG. 5 shows a schematic view of a part of the inside of the outer cup shown in FIGS. 2 and 3.

Instead of manually having to remove the container 1 together with the inner cup 35 from the outer cup 36 and thereby ensure the release of the filter device 15, this process may also be carried out automatically. As shown in FIGS. 3 and 5, this may for example take place by forming a groove 49 in the inside of the outer cup 36. This groove is illustrated in FIG. 3 by means of a dotted line. The groove 49 is designed to interact with a guide pin 50, which is fixed to the inner cup 35 in addition to the squeeze pins, which are not shown in FIG. 3. The groove 49 may have a course as shown in FIG. 5. This course may entail that at first, the guide pin 50 together with the inner cup 35 and the container 1 therein are moved axially downwards in the outer cup 36 until the squeeze pins are activated. During the continued movement of the pin 50, the inner cup 35 is thereafter, moved from a position a (see FIG. 5) to a position b, where the inner cup 35 with the container 1 is placed during the centrifugation until the bloodproduct is produced. When stopping or braking the centrifugation, the pin 50 is moved from position b to position c as a result of the action of the spring 54, and in connection with a resumption of the centrifugation, the pin 50 is now moved further down in the outer cup 36 to the position d. During this moving of the position of the pin 50, the inner cup 35 is turned so far along the inside of the outer cup 36 that the squeeze pins are positioned opposite a groove 51, which is formed in the outer cup 36 and shown by dotted lines in FIG. 5. The position of the squeeze pins 42 opposite this groove 51 means that by means of their respective springs 47, they are disengaged from the container 1 and thereby release the filter device. The centrifugation process continues with the guide pin 50 in the position d shown in FIG. 5 until the filter device has moved up to the surface of the liquid in the container 1.

The groove shown in FIG. 5 may have various shapes, but it must have such a shape that it is ensured that the guide pin 50 is moved along the inside of the outer cup 36 such that the squeeze pins are moved into a groove 51. Appropriately, the groove 51 extends the entire axial length of the inside wall of the outer cup 36 and naturally, there are a number of grooves 51 corresponding to the number of squeeze pins 42 in the inner cup 35.

In a preferred embodiment of the invention, the container is made of polyamide, whereas the other parts are made of polypropylene. The reinforcement mesh may be made of Polyglactine, which is a commonly-used degradable suture material. It may also be made of nylon. Depending on the density, it is placed loosely on top of the filter device or by using light barbs. Alternatively, it may also simply be placed anywhere in the container as due to its density, it may move downwards and into engagement with the blood product during the centrifugation.

In the shown embodiment of the invention, the transverse wall 10 at the top 4 is, as mentioned, designed with a passage 11. Alternatively, the passage 11 may be omitted. In such case, both the penetrable membrane 11 and the transverse wall 10 are penetrated with a needle during the injection of blood. A suitable diameter of the passage 11 is 0.4 mm.

The invention has been described referring to preferred embodiments. Many changes may be made without deviating from the scope of the invention. As an example, the hole-delimiting parts of the mesh may have various cross-sectional shapes, but it is preferred that they have a convex shape on the surface facing the blood product.

The invention claimed is:

1. An apparatus for preparing a multi-layered blood product by centrifugation, said apparatus comprising
    a flexible container comprising a substantially cylindrical body with a closed bottom and a top having a filling opening as well as a filter device, which is slidable inside the container,
    an inner cup adapted to receive the container therein, wherein the inner cup includes holes and squeeze pins positioned adjacent to the bottom of the container, and
    an outer cup capable of receiving the inner cup therein, wherein the outer cup pressing the squeeze pins inward causes the side walls of the container to move radially inwards to releasably affix the filter device at the bottom or in close proximity to the bottom of the container,
    wherein the filter device comprises a substantially planar mesh providing a collecting surface for the blood product during the centrifugation and a supporting buoyancy body, for lifting the blood product collected above or on the mesh of the filter device, to the surface of a liquid in the container during centrifugation of the container.

2. The apparatus according to claim 1, wherein the filling opening being closed by a penetrable membrane, wherein a transverse wall placed between the membrane and the inside of the container and having a small passage.

3. The apparatus according to claim 2, wherein the penetrable membrane has an annular, protruding and plug-like part at the bottom surface thereof, said plug-like part being adapted to face the inside of the container, and that at the side facing the membrane, the transverse wall has an annular flange extending around the passage and interacting with the protruding plug-like part of the membrane in a tight-fitting way.

4. The apparatus according to claim 1, wherein the substantially planar mesh of the filter device has a downwardly extending skirt, and the buoyancy body is a closed capsule, which is received in the cavity defined by the skirt, and that spacing means are provided for fixing the capsule in a distance from both the bottom surface of the mesh and the inner surface of the skirt.

5. The apparatus according to claim 4, wherein the spacing means between the mesh and the buoyancy body are radially extending ribs or rods at the bottom surface of the mesh.

6. The apparatus according to claim 4, wherein the spacing means between the buoyancy body and the skirt are projections at the lateral face of the buoyancy body and are formed with evenly distributed distances relative to each other along the circumference of the buoyancy body.

7. The apparatus according to claim 4, wherein the capsule forming the buoyancy body is formed by two flat-bottomed bowls engaging each other in a telescope-like way with the bottoms facing away from each other, sealing means being provided for tightly sealing the two bowls together.

8. The apparatus according to claim 4, wherein along the periphery, the skirt of the filter device has a number of yielding flaps arranged interspaced and each having a radial protruding projection for frictional interaction with the inner face of the container.

9. The apparatus according to claim 1, wherein the container with the bottom and the top is rotationally-symmetrically shaped around the longitudinal axis of the cylindrical body, and that the top and the cylindrical body including the bottom are separately formed parts, said parts being adapted to be close-fittingly coupled.

10. The apparatus according to claim 4, wherein the mesh of the filter device including the skirt are integrally formed.

11. The apparatus according to claim 1, and where at least the cylindrical body of the container is made of an elastically yielding material, wherein the inner cup and the outer cup are adapted to be inserted into each other with the mouths facing in the same direction, and where the outermost ends of the squeeze pins are adapted to cooperate in a cam follower-like way with the edge of the outer cup when the inner cup and the outer cup are inserted into each other, whereas the inner most ends of the squeeze pins are adapted to press the wall of the container radially inwards when placing the container with the filter device in the inner cup and thereby fix the filter device in close proximity of the bottom of the container until the inner cup and the outer cup are pulled away from each other again.

12. The apparatus according to claim 11, wherein the squeeze pins are spring-preloaded into a radially viewed outer position, wherein their inner ends are level with the inner face of the inner cup.

13. The apparatus according to claim 11, wherein the outer cup is adapted to be a fixed part of a holder for reception of the container during the centrifugation, and that the inner cup and the outer cup are telescoped under the influence of the centrifugal force during the centrifugation.

14. The apparatus according to claim 11, wherein a spring means is provided between the inner cup and the outer cup for moving them automatically away from each other again when stopping the centrifugation.

15. The apparatus according to claim 11, wherein the inside wall of the outer cup is provided with at least one groove for co-operation with a guide pin on the inner cup, so that the inner cup is turned a first distance during a telescoped movement of the inner cup and the outer cup and a subsequent displacement of the inner cup and the outer cup in a direction away from each other again during a first centrifugation phase and is turned a second distance during a second telescoped movement during a subsequent centrifugation phase, and in that in the end, the squeeze pins are placed opposite each their groove in the outer cup, such that they are released and remain unaffected during a continued centrifugation of the container.

16. The apparatus according to claim 11, wherein the outer wall of the inner cup is provided with at least one groove for co-operation with a guide pin on the inner cup, so that the inner cup is turned a first distance during a telescoped movement of the inner cup and the outer cup and a subsequent displacement of the inner cup and the outer cup in a direction away from each other again during a first centrifugation phase and is turned a second distance during a second telescoped movement during a subsequent centrifugation phase, and in that in the end, the squeeze pins are placed opposite each their groove in the outer cup, such that they are released and remain unaffected during a continued centrifugation of the container.

17. The apparatus according to claim 15, wherein the squeeze pins are designed to function as guide pins while interacting with corresponding grooves in the outer cup.

18. The apparatus according to claim 1, wherein at a level above the mesh, the filter device carries an easily releasable reinforcement means for the blood product.

19. The apparatus according to claim 18, wherein the reinforcement means is fixed by means of gravity.

20. The apparatus according to claim 2, wherein the filling opening has the transverse wall placed between the membrane and the inside of the container, said transverse wall having a relatively small, penetrable wall thickness.

* * * * *